United States Patent [19]

Renken

[11] Patent Number: 4,642,303

[45] Date of Patent: Feb. 10, 1987

[54] CATALYST COMPOSITION

[75] Inventor: Terry L. Renken, Austin, Tex.

[73] Assignee: Texaco Inc., White Plains, N.Y.

[21] Appl. No.: 813,884

[22] Filed: Dec. 27, 1985

[51] Int. Cl.$^4$ .......................... B01J 23/72; B01J 23/86
[52] U.S. Cl. .................................. 502/315; 544/106;
544/404; 564/503; 564/506; 564/507
[58] Field of Search .............................. 502/315, 316

[56] References Cited

U.S. PATENT DOCUMENTS

| | | | |
|---|---|---|---|
| 3,037,025 | 5/1962 | Godfrey | 564/503 X |
| 3,151,112 | 9/1964 | Moss | 544/106 |
| 3,152,998 | 10/1964 | Moss | 502/315 |
| 3,928,241 | 12/1975 | Niimi et al. | 502/315 |

Primary Examiner—W. J. Shine
Attorney, Agent, or Firm—Jack H. Park; Kenneth R. Priem; Carl G. Ries

[57] ABSTRACT

The present invention is directed to catalyst compositions containing nickel, copper, chromium and iron which are useful for promoting reductive amination reactions, such as the conversion of feedstocks containing one or more hydroxyl groups to corresponding amine compounds including acyclic, cyclic and heterocyclic amines. For example, the catalyst compositions of the present invention may be utilized to convert monoethanolamine to ethylenediamine and piperazine, for the conversion of diethylene glycol to morpholine and diglycolamine, etc.

3 Claims, No Drawings

CATALYST COMPOSITION

BACKGROUND OF THE INVENTION

1. Technical Field of the Invention

This invention relates to novel catalyst compositions containing nickel, copper, iron and chromia. More particularly, this invention relates to novel catalyst compositions containing from about 1 to about 20 wt. % of iron and from about 1 to about 6 wt. % of chromia, the balance being nickel and copper in the weight ratio of about 2 to 3 parts of nickel per part of copper.

The invention is based upon the discovery that the inclusion of iron in a catalyst composition containing nickel, copper and chromia results in the provision of catalyst compositions having good stability and enhanced activity.

2. Prior Art

Godfrey U.S. Pat. No. 3,037,025 discloses the preparation of N-alkyl substituted piperazines using catalyst compositions consisting of the metals and oxides of copper, nickel and cobalt (including mixtures thereof) which may also be promoted by the inclusion of a normally non-reducible metal oxide such as chromium, aluminum, iron, calcium, magnesium, manganese and the rare earths. Preferred catalyst compositions are indicated as containing from about 44 to about 74 wt. % of nickel, about 5 to about 55 wt. % of copper and about 1 to about 5 wt. % of chromia.

Moss U.S. Pat. No. 3,151,112 discloses catalyst compositions useful for the preparation of morpholines including one or more metals from the group including copper, nickel, cobalt, chromium, molybdenum, manganese, platinum, palladium and rhodium, which may also be promoted with normally nonreducible oxides such as chromium oxide, molybdenum oxide and manganese oxide. Representative catalyst compositions include those containing from about 60 to about 85 wt. % of nickel, about 14 to about 37 wt. % of copper and about 1 to about 5 wt. % of chromia. Nickel, copper, chromia catalysts are also disclosed in Moss U.S. Pat. No. 3,151,115 and Moss U.S. Pat. No. 3,152,998.

Winderl et al. U.S. Pat. No. 3,270,059 teaches the use of catalysts containing a metal of groups I-B and VIII of the Periodic System. Examples of suitable catalysts are stated to be copper, silver, iron, nickel, and particularly, cobalt.

Boettger et al. U.S. Pat. No. 4,014,933 discloses catalysts containing cobalt and nickel promoted with copper such as those containing from about 70 to about 95 wt. % of a mixture of cobalt and nickel and from about 5 to about 30 wt. % of copper.

Habermann U.S. Pat. No. 4,152,353 discloses catalyst compositions comprising nickel, copper and a third component which may be iron, zinc, zirconium or a mixture thereof such as catalysts containing from about 20 to about 49 wt. % of nickel, about 36 to about 79 wt. % of copper and about 1 to about 15 wt. % of iron, zinc, zirconium or a mixture thereof. Similar catalyst compositions are mentioned in Habermann U.S. Pat. No. 4,153,581.

European patent application No. 0017651 filed Oct. 20, 1980, contains a disclosure of catalyst compositions related to those disclosed by Habermann, such catalyst compositions being composed of nickel or cobalt, copper and iron, and zinc or zirconium such as compositions containing 20 to 90% cobalt, 3 to 72% copper and 1 to 16% of iron, zinc or zirconium and catalyst compositions containing 20 to 49% nickel, 36 to 79% copper and 1 to 16% of iron, zinc or zirconium.

German Offen. No. 2,721,033 discloses a catalyst composition containing 35% nickel, about 87.5% iron and a minor amount of chromia.

Johansson et al. U.S. Pat. No. 3,766,184 discloses catalyst compositions composed of iron and nickel and/or cobalt.

SUMMARY OF THE INVENTION

The present invention is directed to catalyst compositions containing nickel, copper, chromia and iron which are useful for promoting reductive amination reactions, such as the conversion of feedstocks containing one or more hydroxyl groups to corresponding amine compounds including acyclic, cyclic and heterocyclic amines. For example, the catalyst compositions of the present invention may be utilized to convert monoethanolamine to ethylenediamine and piperazine, for the conversion of diethylene glycol to morpholine and 2-(2-aminoethoxy)ethanol.

The catalyst compositions of the present invention are characterized by a high level of activity for reductive amination reactions coupled with good catalyst stability and good selectivity to desired products.

The catalyst compositions of the present invention consist essentially of nickel, copper, chromia and iron in the proportions of about 1 to about 20 wt. % of iron, about 1 to about 6 wt. % of chromia and with the balance being nickel and copper in the weight ratio of about 2 to 3 parts of nickel per part of copper. For example, the catalyst compositions of the present invention may consist essentially of about 40 to about 60 wt. % of nickel, about 20 to about 40 wt. % of copper, about 1 to about 6 wt. % of chromia and about 1 to about 20 wt. % of iron, with the metals being proportioned as indicated above.

More preferably, the catalyst compositions of the present invention will contain about 1 to about 15 wt. % of iron and about 1 to about 5 wt. % of chromia, with the metals being proportional as indicated above.

Although the catalyst compositions of the present invention may be utilized in powdered form in conducting batch reactions, their utility is enhanced when they are used in pelleted form for catalyzing continuous reductive amination reactions. When a catalyst is used in pelleted form for a continuous reaction, it is necessary that the pellets have good physical and chemical properties so that they will not disintegrate or break during the course of the continuous reductive amination reaction. The catalyst compositions of the present invention have such properties.

SPECIFIC EXAMPLES

Catalyst Preparations

The first step in a typical catalyst preparation involved the coprecipitation of metal carbonates from aqueous solution. Hot solutions (60°–70° C.), one of which contained a mixture of metal nitrate salts and the other sodium carbonate, were added simultaneously to the stirred mixture at rates so as to maintain the pH at 7–8. The precipitate was filtered and then washed several times by slurring with fresh deionized water heated to 60° C., followed by filtration. The material was then dried at 110°–140° C., calcined at 400° C. to produce the metal oxides and then reduced with hydrogen at 280°–300° C. The catalysts were then stabilized to the atmosphere by partial oxidation with a dilute oxygen stream.

Several catalysts containing Ni, Cu and Cr with and without Fe were prepared. Portions of the catalyst powders were tableted for testing in the continuous fixed bed amination experiments.

Batch Monoethanolamine Amination Experiments

Catalysts were tested for activity in the batch amination of monoethanolamine (MEA) to produce ethylenediamine and piperazine as the major products. The general procedure was to charge 25 g of MEA and 2.5 g of powdered catalyst to a glass liner in a rocking autoclave. The clave was sealed, flushed with hydrogen and then 42 g of ammonia was added. The system was pressured to 500 psig with hydrogen and then heated to 210° C. for 2 hours with rocking. The liquid contents of the clave were analyzed by gas chromatography.

The % MEA conversions were calculated for each of the runs and are given in the following table. Also given are the corresponding bulk metal catalyst compositions and the pellet diameter and length used in the continuous runs described later.

| Ex. | Pellet Size, in. | Wt % Metals | | | | %MEA Conversion | % EDA | % PIP |
|---|---|---|---|---|---|---|---|---|
| | | Ni | Cu | Cr | Fe | | | |
| 1 | 5/32 | 61.8 | 24.3 | 2.6 | — | 35.1 | 62.5 | 11.8 |
| 2 | 5/32 | 54.4 | 22.9 | 5.2 | — | 26.3 | 61.2 | 10.5 |
| 3 | ⅛ | 68 | 20 | 1.5 | — | 38.3 | 57.7 | 18.2 |
| 4 | 5/32 | 46.3 | 18.4 | 4.6 | 6.8 | 86.0 | 43.2 | 33.0 |
| 5 | 5/32 | 49.9 | 16.9 | 4.7 | 12.8 | 77.0 | 43.2 | 30.4 |
| 6 | 5/32 | 45.3 | 26.7 | 3.5 | 9.9 | — | — | — |

As can be seen from the data in this table, the incorporation of Fe into the Ni-Cu-Cr catalyst system produced catalysts with greatly increased activities in the amination of MEA. The iron was incorporated at the outset of the preparations by including iron salt in the coprecipitation step, followed by the standard procedures. The exact nature of this increased activity is not known, but it probably results from increased surface area of the active catalyst.

Continuous Amination Experiments

Continuous monoethanolamine (MEA) amination runs were carried out in an upward flow tubular 100 cc stainless steel reactor equipped with both continuous liquid and hydrogen feed capabilities. Pelleted catalyst (50–100 cc) was charged to the reactor for each of the runs. MEA and ammonia were pumped through the catalyst bed at total space velocities of 3–5 g/hr-cc catalyst in ammonia:MEA molar ratios of approximately 6:1. The reactor pressure was maintained at 2500 psig in all the examples. Reactor effluent samples were analyzed by gas chromatography on an ammonia and water free basis. Results of theses analyses along with the appropriate reactor conditions are given in the following examples.

EXAMPLE 1

Ni-Cu-Cr Catalyst

| Reactor Temp., °C. | 170 | 180 | 190 | 200 | 210 |
|---|---|---|---|---|---|
| LHSV, g/hr-cc cat. | 4.9 | 5.1 | 5.0 | 5.4 | 5.5 |
| Mol NH$_3$/mol MEA | 5.7 | 6.2 | 6.3 | 5.4 | 5.3 |
| H$_2$, SCF/lb MEA | .17 | .17 | .18 | .15 | .14 |
| % MEA coversion | 21.7 | 33.5 | 49.1 | 56.2 | 72.1 |
| % Selectivities: EDA | 74.8 | 71.4 | 62.1 | 56.1 | 41.1 |
| Piperazine | 7.8 | 9.5 | 17.4 | 21.8 | 32.1 |

EXAMPLE 2

Ni-Cu-Cr Catalyst

| Reactor Temp., °C. | 180 | 190 | 200 | 210 |
|---|---|---|---|---|
| LHSV, g/hr-cc cat. | 5.1 | 5.3 | 5.1 | 5.1 |
| Mol NH$_3$/mol MEA | 6.1 | 6.0 | 5.9 | 5.9 |
| H$_2$, SCF/lb MEA | 0.18 | 0.17 | 0.17 | 0.17 |
| % MEA conversion | 17.5 | 34.2 | 51.3 | 67.2 |
| % Selectivities: EDA | 74.1 | 67.1 | 60.1 | 49.8 |
| Piperazine | 4.2 | 10.3 | 16.1 | 24.7 |

EXAMPLE 3

Ni-Cu-Cr Catalyst

| Reactor Temp., °C. | 180 | 190 | 200 |
|---|---|---|---|
| LHSV, g/hr-cc cat. | 4.0 | 4.0 | 4.0 |
| Mol NH$_3$/mol MEA | 6.0 | 6.0 | 6.0 |
| H$_2$, SCF/lb MEA | 0.15 | 0.15 | 0.15 |
| % MEA conversion | 29.1 | 45.0 | 67.0 |
| % Selectivities: EDA | 84.3 | 80.9 | 62.5 |
| Piperazine | 5.6 | 11.0 | 23.8 |

EXAMPLE 4

Ni-Cu-Cr-Fe Catalyst

| Reactor Temp., °C. | 180 | 190 | 200 | 210 |
|---|---|---|---|---|
| LHSV, g/hr-cc cat. | 3.5 | 2.7 | 3.7 | 2.7 |
| Mol NH$_3$/mol MEA | 5.3 | 6.2 | 4.9 | 5.9 |
| H$_2$, SCF/lb MEA | 0.15 | 0.22 | 0.14 | 0.21 |
| % MEA conversion | 52.0 | 82.5 | 82.0 | 88.7 |
| % Selectivities: EDA | 57.1 | 45.2 | 43.1 | 30.5 |
| Piperazine | 19.1 | 31.4 | 35.2 | 42.2 |

EXAMPLE 5

Ni-Cu-Cr-Fe Catalyst

| Reactor Temp., °C. | 180 | 190 | 200 |
|---|---|---|---|
| LHSV, g/hr-cc cat. | 4.3 | 4.0 | 3.9 |
| Mol NH$_3$/mol MEA | 6.0 | 6.0 | 6.0 |
| H$_2$, SCF/lb MEA | 0.15 | 0.16 | 0.17 |
| % MEA conversion | 44.7 | 70.1 | 77.1 |
| % Selectivities: EDA | 59.8 | 58.3 | 47.0 |
| Piperazine | 16.2 | 19.3 | 28.1 |

In general, the physical stabilities of the unsupported Ni-Cu-Cr and Ni-Cu-Cr-Fe catalysts were found to be good. Mostly whole pellets were recovered from the reactor after the runs.

Supported Ni-Cu-Cr and Ni-Cu-Cr-Fe on kieselguhr catalysts were also tested in continuous MEA amination using the same amination procedures as described above. The catalysts were prepared using similar procedures as those described for the unsupported catalysts except that the coprecipitations were done in the presence of kieselguhr. The results of the experiments are given in Examples 6 and 7. The catalyst of Example 6 contained 48.0% Ni, 15.0% Cu and 1.1% Cr. The catalyst of Example 8 contained 44.4% Ni, 12.4% Cu, 1.0% Cr and 3.0% Fe.

EXAMPLE 6

Ni-Cu-Cr/kgr Catalyst

| Reactor Temp., °C. | 190 | 200 |
| --- | --- | --- |
| LHSV, g/hr-cc cat. | 4.2 | 4.2 |
| Mol NH$_3$/mol MEA | 6.1 | 6.2 |
| H$_2$, SCF/lb MEA | 2.21 | 2.23 |
| % MEA conversion | 28.1 | 41.4 |
| % Selectivities: EDA | 64.8 | 58.4 |
| Piperazine | 10.0 | 16.5 |

EXAMPLE 7

Ni-Cu-Cr-Fe/kgr Catalyst

| Reactor Temp., °C. | 190 | 200 |
| --- | --- | --- |
| LHSV, g/hr-cc cat. | 3.8 | 3.8 |
| Mol NH$_3$/mol MEA | 6.0 | 6.0 |
| H$_2$, SCF/lb MEA | 2.25 | 2.27 |
| % MEA conversion | 44.5 | 62.1 |
| % Selectivities: EDA | 75.5 | 65.2 |
| Piperazine | 11.1 | 19.1 |

As can be seen in comparing the results given in Examples 6 and 7, the iron containing catalyst was significantly more active than the catalyst which contained no iron, as exhibited by the increased MEA conversions.

It will be understood that the foregoing examples are given by way of illustration and not by way of limitation and that the scope of the present invention is defined solely by the appended claims.

I claim:

1. A catalyst composition consisting essentially of nickel, copper, chromia and iron, said composition containing nickel and copper in the weight ratio of about 2 to 3 parts of nickel per part of copper and also containing, based on the total weight of the composition, from about 1 to about 20 wt. % of iron and from about 1 to about 6 wt. % of chromia.

2. A catalyst composition as in claim 1 containing from about 40 to about 60 wt. % of nickel, from about 20 to about 40 wt. % of copper, from about 1 to about 6 wt. % of chromia and from about 1 to about 20 wt. % or iron.

3. A catalyst composition as in claim 2 containing from about 1 to about 5 wt. % of chromia and from about 1 to about 15 wt. % of iron.

* * * * *